United States Patent
Kong et al.

(10) Patent No.: US 11,458,221 B2
(45) Date of Patent: Oct. 4, 2022

(54) DIATOM MICROBUBBLER FOR BIOFILM REMOVAL

(71) Applicant: The Board of Trustees of the University of Illinois, Urbana, IL (US)

(72) Inventors: Hyunjoon Kong, Champaign, IL (US); Yongbeom Seo, Woodbury, MN (US); Jiayu Leong, Singapore (SG); Yu-Heng Deng, Urbana, IL (US)

(73) Assignee: BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 542 days.

(21) Appl. No.: 16/540,291

(22) Filed: Aug. 14, 2019

(65) Prior Publication Data

US 2020/0093947 A1    Mar. 26, 2020

Related U.S. Application Data

(60) Provisional application No. 62/733,628, filed on Sep. 20, 2018.

(51) Int. Cl.

| | |
|---|---|
| *C23F 11/18* | (2006.01) |
| *A61K 38/54* | (2006.01) |
| *A61L 2/18* | (2006.01) |
| *A61L 2/26* | (2006.01) |
| *B01J 35/02* | (2006.01) |
| *B01J 21/08* | (2006.01) |
| *B01J 35/00* | (2006.01) |
| *B01J 23/34* | (2006.01) |

(52) U.S. Cl.
CPC ............ *A61L 2/186* (2013.01); *A61L 2/26* (2013.01); *B01J 21/08* (2013.01); *B01J 23/34* (2013.01); *B01J 35/0006* (2013.01); *B01J 35/02* (2013.01)

(58) Field of Classification Search
CPC ....... C02F 3/107; C02F 2303/20; B01J 35/02; A61L 2/186; A61L 2/0088; A61L 2202/13; A61L 2101/12; A61L 2101/24; A61L 2101/26; A61L 2101/30
USPC .......................................... 422/18; 424/94.2
See application file for complete search history.

(56) References Cited

U.S. PATENT DOCUMENTS

| | | | |
|---|---|---|---|
| 2010/0233146 A1* | 9/2010 | McDaniel ............... | C09D 5/14 435/174 |
| 2012/0003146 A1* | 1/2012 | Fliermans ............... | C01B 6/00 977/773 |
| 2018/0056248 A1* | 3/2018 | Guha .................... | B01D 71/56 |

* cited by examiner

*Primary Examiner* — Monzer R Chorbaji
(74) *Attorney, Agent, or Firm* — DLA Piper LLP US

(57) ABSTRACT

Diatom microbubblers comprising diatom biosilica or other silica linked to a catalyst for the decomposition of hydrogen peroxide, such as manganese oxide ($MnO_2$), platinum (Pt), CuO (copper II oxide), or zinc peroxide ($ZnO_2$) particles or nanosheets, or catalase are provided. Further provided are methods of reducing or eliminating biofilm or biofouling conditions.

22 Claims, 12 Drawing Sheets
(12 of 12 Drawing Sheet(s) Filed in Color)

DIATOM MICROBUBBLER FOR BIOFILM REMOVAL

PRIORITY

This application claims the benefit of U.S. Ser. No. 62/733,638, filed Sep. 20, 2018, which is incorporated by reference in its entirety herein.

STATEMENT REGARDING FEDERALLY SPONSORED RESEARCH OR DEVELOPMENT

This invention was made with government support under 1R01 HL109192 and 1R21 HL131469, awarded by the National Institutes of Health, and CBET-0939511, awarded by the National Science Foundation. The government has certain rights in the invention.

BACKGROUND

Microbial biofilms form on and within many living tissues, medical devices, and engineered materials, threatening human health and sustainability. Removing biofilms remains a grand challenge despite tremendous efforts made so far, particularly when they are formed in confined spaces. One primary cause is the limited transport of anti-bacterial agents into extracellular polymeric substances (EPS) of the biofilm or biofouling condition.

Biofilms are communities of microbial cells that are prevalent in many materials such as medical devices, injured/diseased living tissues, household products, and infrastructure. Multiple microbial cells build the biofilm by accumulating on solid-liquid interfaces and producing a protective matrix of extracellular polymeric substances (EPS), which includes various biomolecules, such as oligopeptides, lipopolysaccharides, proteins, lipids, and DNA. The resulting biofilms impact public health, product function, and infrastructure sustainability significantly. About 80% of all medical infections originate from biofilms of pathogens. Therefore, tremendous efforts have been conducted to remove biofilms from the substrates using various antibiotics and disinfectants. However, bacterial cells residing in biofilms are deemed 100 to 1,000 times more resistant to antibiotics and disinfecting agents than planktonic cells because the EPS matrix limits the transport of the antimicrobial agents and neutralizes them chemically. Furthermore, the biofilm formed in confined spaces are even more challenging to eliminate using conventional methods than that on the open surface because the biofilm matrix becomes even sturdier and denser.

SUMMARY

Provided herein are biosilica microbubblers comprising diatom biosilica (or other silica structures) linked to a catalyst for the decomposition of hydrogen peroxide ($H_2O_2$). In an embodiment the catalyst for the decomposition of hydrogen peroxide is (1) manganese oxide ($MnO_2$), platinum (Pt), CuO (copper II oxide), or zinc peroxide ($ZnO_2$) particles or nanosheets, or (2) catalase. The diatom biosilica can be linked to $MnO_2$ nanosheets. The diatom biosilica can be linked to $MnO_2$ via a polydopamine linker. The diatom biosilica can be cylinder-shaped with a hollow central bore.

Another embodiment provides a method of reducing a biofilm or biofouling condition. The method comprises contacting a diatom microbubbler comprising diatom biosilica linked to a catalyst for the decomposition of $H_2O_2$ and a $H_2O_2$ solution with the biofilm or biofouling condition for a period effective to reduce reproduction of microorganism or to reduce numbers of microorganisms in or on the biofilm or biofouling condition. The catalyst for the decomposition of hydrogen peroxide can be, for example, (1) manganese oxide ($MnO_2$), platinum (Pt), CuO (copper II oxide), or zinc peroxide ($ZnO_2$) particles or nanosheets, or (2) catalase. The method can be performed a second time with a fresh diatom microbubbler and fresh $H_2O_2$ solution. The $H_2O_2$ solution can be an about 1% to about 5% solution of $H_2O_2$. The diatom microbubbler can be present at a concentration of about 0.5 to about 5.0 mg mL$^{-1}$. The diatom microbubbler can be mixed with the $H_2O_2$ and then contacted with the biofilm or biofouling condition. Alternatively, the diatom microbubbler and the $H_2O_2$ can be contacted separately with the biofilm or biofouling condition. The biofilm or biofouling condition can comprise one or more strains of bacteria, fungi, filamentous fungi, yeasts, algae, cyanobacteria, viruses, and protozoa and combinations thereof. The biofilm or biofouling condition can comprise one or more strains of bacteria. The biofilm or biofouling condition can be present in or on a non-living surface or in or on a living surface or organism. The organism can be a human or a mammal. The biofilm can be present at a wound site or infection site in a mammal. The storage modulus of the biofilm or biofouling condition can be reduced by 50% or more. The amount of extracellular polymeric substances (EPS) of the biofilm can be reduced by 50% or more.

Yet another embodiment provides a method for making amine-substituted diatom biosilica particles. The method comprises contacting diatom biosilica and dopamine hydrochloride with water and stirring to form a solution. Tris-buffer is added to the solution and stirred until amine-substituted diatom biosilica particles are formed. The amine-substituted diatom biosilica particles are collected.

Microparticles engineered to be self-locomotive with microbubbles can clean a structure fouled by biofilm by fracturing the EPS and subsequently improving transport of an antiseptic reagent. Microparticles such as hollow cylinder-shaped diatom biosilica doped with a catalyst for the decomposition of hydrogen peroxide can be used to make a diatom microbubbler. In an antiseptic solution, such as an $H_2O_2$ solution, microparticles doped by a catalyst for the decomposition of hydrogen peroxide can discharge oxygen gas bubbles continuously and become self-motile. The microparticles can infiltrate a bacterial biofilm formed and continued to generate microbubbles. The resulting microbubbles can merge and convert surface energy to mechanical energy high enough to fracture the matrix of biofilm. Consequently, $H_2O_2$ molecules can diffuse into the biofilm and kill most microbial cells. Overall, the compositions and methods described herein can provide a unique and powerful tool that can significantly impact current efforts to clean a wide array of bio-fouled products and devices.

BRIEF DESCRIPTION OF THE FIGURES

The patent or application file contains at least one drawing executed in color. Copies of this patent or patent application publication with color drawings will be provided by the Office upon request and payment of the necessary fee.

DETAILED DESCRIPTION

Figure 1:
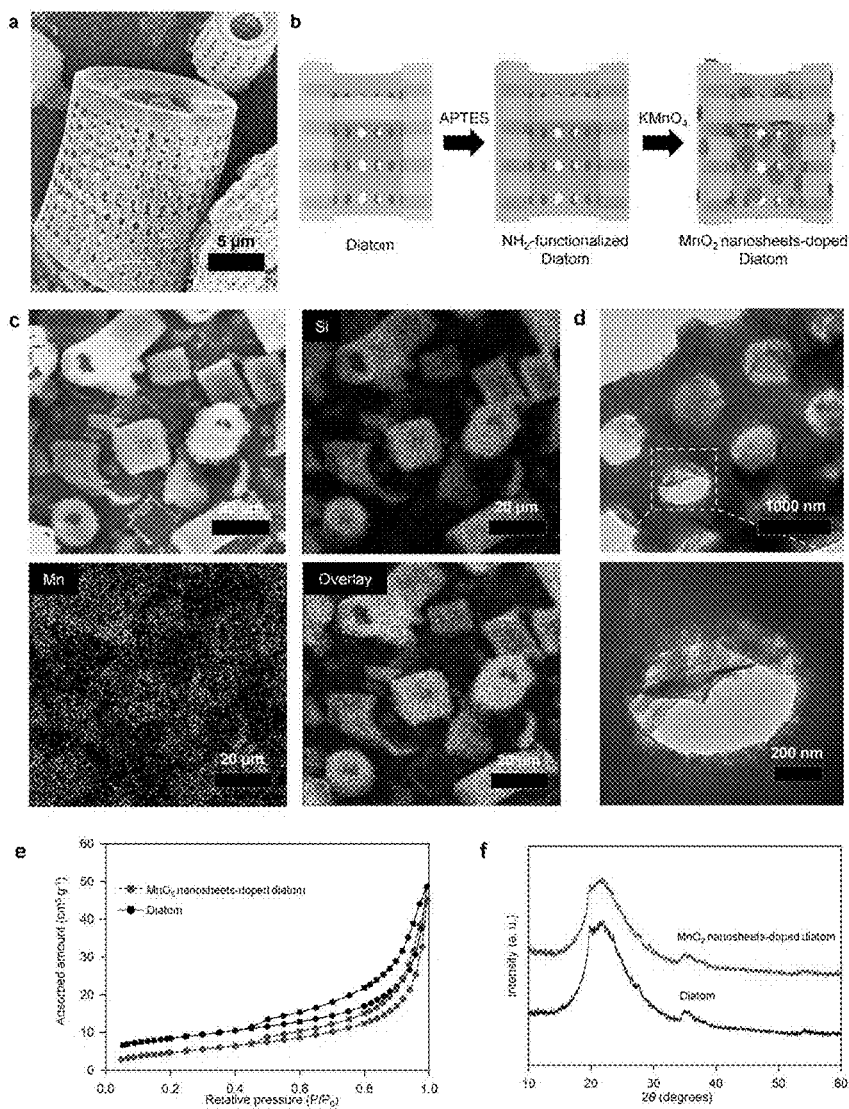
FIG. 1. Fabrication and characterization of the $MnO_2$ nanosheets-doped diatom. (a) SEM image of diatom. (b) Schematic illustration of fabrication steps for $MnO_2$ nanosheets-doped diatom. (c) Elemental mapping images showing homogenous distribution of $MnO_2$ nanosheets on diatom. (d) High-resolution TEM image of MnO$_2$ nanosheets on diatom. (e, f) Nitrogen adsorption-desorption isotherms (e) and powder X-ray diffraction patterns (f) of diatom and MnO$_2$ nanosheets-doped diatom.

The compositions and methods are more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The term "about" in association with a numerical value means that the value varies up or down by 5%. For example, for a value of about 100, means 95 to 105 (or any value between 95 and 105). All patents, patent applications, and other scientific or technical writings referred to anywhere herein are incorporated by reference herein in their entirety.

Provided herein are microparticles assembled to generate microbubbles and self-propel in the anti-bacterial solutions, such as H$_2$O$_2$ solutions and act as an active cleaning agent. Due to the small size and active movement, the particles are able to penetrate an EPS matrix of biofilm and continue to generate microbubbles inside the biofilm. The resulting microbubbles give rise to a wave of mechanical energy high enough to deform the biofilm. In turn, H$_2$O$_2$ molecules can diffuse into the biofilm matrix and eradicate microbial cells. In an embodiment a catalyst for the decomposition of hydrogen peroxide, such as manganese oxide (MnO$_2$) nanosheets, are bound to diatom biosilica, which is a skeleton of dead algae. A catalyst for the decomposition of hydrogen peroxide can generate oxygen ($O_2$) bubbles by decomposing $H_2O_2$. A porous and cylindrical geometry of diatom can be used to facilitate the diffusion of $H_2O_2$.

Diatom Silica

Any type of diatom silica can be used herein. In one embodiment diatom silica particles can have a hollow cylinder morphology. That is, a cylindrical shape with a hollow bore. It is noted, however, that other morphologies can be used. In an embodiment diatom silica is about 5, 10, 20, 30, 40 µm or more diameter. In an embodiment, diatom silica is about 5, 10, 15, 18, 20, 25, 30, 40 µm or more length. Walls of the diatom silica can have pores. In an embodiment the walls can have a multitude of pores with an average diameter of about 100, 200, 300, 400, 500, 600, 700, 800, 900 nm or more.

Man-made silica forms similar to diatom silica described herein can be used in place of diatom silica. Methods of making porous silica forms are well known in the art.

Catalyst for Decomposition of Hydrogen Peroxide

In an embodiment, a catalyst for the decomposition of hydrogen peroxide is linked to diatom silica. In an embodiment $MnO_2$, Pt, CuO, or $ZnO_2$ particles or nanosheets as well as catalase can be linked to diatom silica. $MnO_2$ nanosheets are redox active two dimensional nanomaterials that have thicknesses on the nanometer scale or smaller. The lateral size of $MnO_2$ nanosheets can range from sub-micrometers to micrometers. $MnO_2$ nanosheets have three atomic layers: one Mn layer sandwiched by two O layers. Each Mn coordinates to six O atoms to form edge-sharing $MnO_6$ octahedra. $MnO_2$ nanosheets are negatively charged and repulsive to each other. The d-d transitions of Mn ions in the $MnO_6$ octahedra of $MnO_2$ nanosheets result in a broad absorption spectrum (about 200-600 nm) with a large molar extinction coefficient ($\varepsilon_{max}=9.6\times10^3$ $M^{-1}$ $cm^{-1}$) at 380 nm. Several methods of making these types of nanosheets are known in the art.

Linkages

Diatom silica can be functionalized with, for example amine groups, so that they can be linked to a catalyst for the decomposition of hydrogen peroxide such as catalase, particles, or nanosheets, such as $MnO_2$ nanosheets. However, any suitable linkage or bond can be used. For example, —COOH chealating, electodeposition, or hydrothermal reactions (direct deposition) can be used to link $MnO_2$, Pt, CuO, or $ZnO_2$ particles or nanosheets as well as catalase to diatom silica. In an embodiment polydopamine or polymers substituted with dopamine groups can be used as a linker to immobilize $MnO_2$, Pt, CuO, or $ZnO_2$ particles or nanosheets as well as catalase to diatom silica. In an embodiment, a catalyst for the decomposition of hydrogen peroxide can be immobilized or linked to diatom silica or other silica by covalent bonding, ionic bonding, hydrogen bonding, hydrophobic bonding, adsorption, or affinity bonding.

Biofilms and Biofouling

The methods and compositions described herein can be used to ameliorate, reduce, remove, or prevent biofouling or biofilms. Biofouling is the undesirable accumulation of microorganisms, such as bacteria on structures exposed to solvent. Biofouling can occur, for example on the hulls of ships, in membrane systems, such as membrane bioreactors and reverse osmosis spiral wound membranes, water cooling systems of large industrial equipment and power stations, and oil pipelines carrying, e.g., used oils, cutting oils, soluble oils or hydraulic oils.

A biofilm can cause biofouling and is an aggregate of organisms wherein the organisms are adhered to each other, to a surface, or a combination thereof. A biofilm can comprise one or more species of bacteria, fungi, filamentous fungi, yeasts, algae, cyanobacteria, viruses, and protozoa and combinations thereof. Microorganisms present in a biofilm can be embedded within a self-produced matrix of extracellular polymeric substances. When a microorganism switches to a biofilm mode of growth, it can undergo a phenotypic shift in behavior wherein large suites of genes are differentially regulated. Nearly every species of microorganism can form biofilms.

Biofilms can be found on or in living organisms or in or on non-living structures. Biofilms can be present on structures contained in naturally occurring bodies of water or man-made bodies of water, on the surface of water, surfaces exposed to moisture, interiors of pipes, cooling water systems, marine systems, boat hulls, on teeth and oral surfaces, on plant surfaces, inside plants, on human and animal body surfaces, inside humans and animals, on contact lenses, on catheters, prosthetic cardiac valves, other prosthesis, intrauterine devices, and other medical structures/devices.

Biofilms can cause corrosion of metal surfaces, inhibit vessel speed, cause plant diseases, and can cause human and animal diseases. Biofilms are involved in human and animal infections, including, for example, urinary tract infections, catheter infections, middle-ear infections, dental plaque, gingivitis, dental caries, dental enamel, periodontal diseases, oral wounds, endocarditis, infections in cystic fibrosis, chronic sinusitis, and infections of permanent indwelling devices such as joint prostheses and heart valves. Biofilms can also impair cutaneous wound healing and reduce topical antibacterial efficiency in healing or treating infected skin wounds. Therefore, the compositions and methods described herein can be used to treat or prevent these human and animal infections and wounds via application of the diatom microbubblers and antiseptic reagents to the site of the infection or wound.

Some microorganisms that can form biofilms, cause biofouling and/or cause disease in humans and animals include, for example, bacteria, fungi, yeast, algae, protozoa, and viruses as described above. Biofilms can be treated in living organisms by applying the microparticle microbubblers and an antiseptic reagent such as $H_2O_2$ to cells, tissues, or organs of the living organism. Biofilms and biofouling conditions on non-living surfaces can be treated by applying the diatom microbubblers and antiseptic reagent onto the non-living surface or to the area surrounding the surface. Diatom microbubblers can also be added to the water, oil, or other fluid surrounding and in contact with the non-living surface.

One embodiment provides methods of ameliorating or preventing a biofouling condition or a biofilm condition, caused by one or more microorganisms, such as bacteria. The methods comprise administering diatom microbubblers and an antiseptic reagent to the biofouling condition or biofilm condition, wherein the biofouling condition or biofilm condition is ameliorated.

Diatom microbubblers and an antiseptic reagent can be administered to a surface that has a biofilm or biofouling condition or can be administered to a surface as a prophylactic measure.

Where the biofilm is present or potentially present on an artificial surface within a human or animal (e.g., a catheter or medical device), the artificial surface can be contacted with diatom microbubblers and an antiseptic reagent prior to insertion into the human or animal or can be delivered to the surface after the artificial surface is inserted into the human or animal.

Methods

Figure 4:
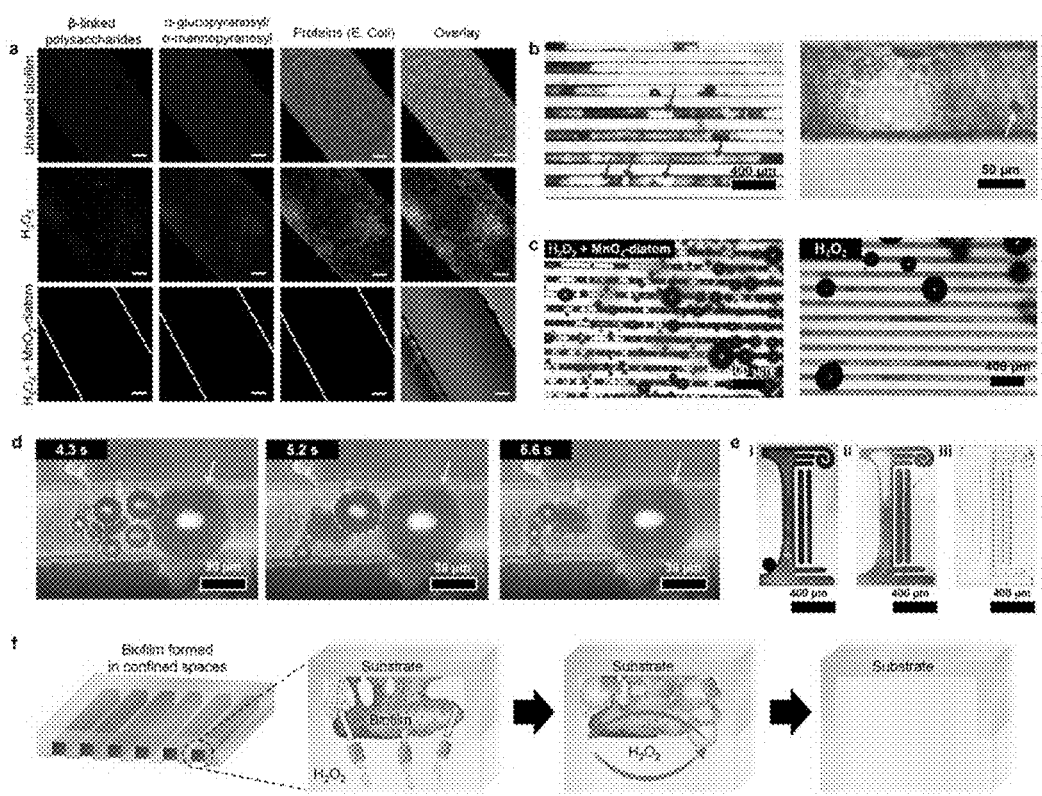
FIG. 4. Mechanistic study of the active biofilm removal using MnO$_2$-diatom bubbler. (a) Fluorescent images of the β-linked polysaccharides (blue), α-glucopyranoayl/α-mannopyranosyl polysaccharides (red), and extracellular proteins (green) in extracellular polymer substances. (Scale bar=10 μm). (b) Optical image of the intermediate stage of biofilm removal using MnO$_2$-diatom. Red and yellow arrows indicate the cleaned area in microgrooves by microbubbles and the invaded MnO$_2$-diatom particles in biofilm matrix, respectively. (c) Optical images of the biofilm captured after 5 minutes of exposure to 3% H$_2$O$_2$ solution with and without MnO$_2$-diatom. (d) Time-lapse image of microbubbles within the grooves. Smaller microbubbles (dot circles) merge into a big bubble (yellow arrows), which collapses eventually. (e) Optical images of (i) the biofilm formed in the PDMS substrate with complex micropattern (i), and the biofilm treated by 3% H$_2$O$_2$ solution without (ii) and with MnO$_2$-diatom (iii). (f) Schematic illustration of the active cleaning mechanism.
Figure 12:
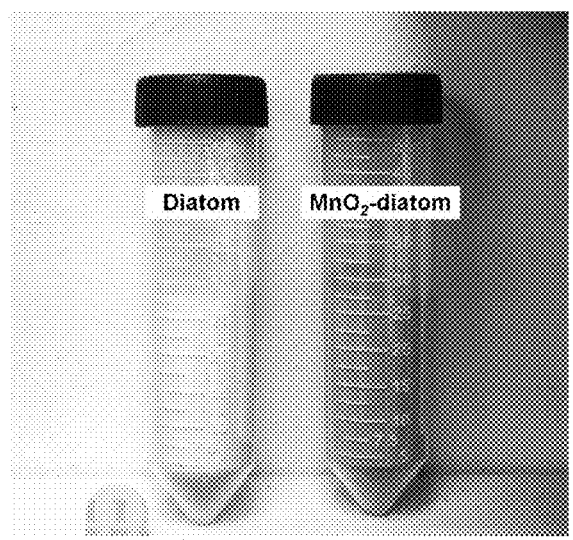
FIG. 12. Scaled-up fabrication (10 g) of the MnO$_2$-diatom with 98% yield.

Microparticles, such as diatoms, can be engineered to generate microbubbles and self-propel to invade and damage biofilms (FIG. 4f). In an antiseptic $H_2O_2$ solution, diatoms doped by a catalyst for the decomposition of hydrogen peroxide, such as $MnO_2$ nanosheets, can infiltrate a biofilm by microbubble propulsion. The microparticles invading the biofilm continue to generate microbubbles that merge to deform and ultimately fracture the EPS matrix of biofilm. Then, $H_2O_2$ molecules can diffuse into the biofilm more actively and induce microbial cell death more efficiently than those free of the diatom bubbler as observed with the decrease in the cell viability over time. Since diatoms are abundant in nature, diatoms doped with $MnO_2$ nanosheets can readily be produced on a large scale (FIG. 12). The methods therefore provide for effective an active anti-biofilm system in biomedical and environmental applications.

Provided herein are methods of reducing a biofilm or biofouling condition. The methods comprise contacting: a diatom microbubbler comprising diatom biosilica linked to a catalyst for the decomposition of hydrogen peroxide, such as manganese oxide ($MnO_2$), platinum (Pt), CuO (copper II oxide), or zinc peroxide ($ZnO_2$) particles or nanosheets, or catalase; and a $H_2O_2$ solution; with the biofilm or biofouling condition for a period effective to reduce reproduction of microorganism or to reduce numbers of microorganisms in or on the biofilm or biofouling condition. The contact time can be about 0.5, 1, 5, 10, 30, 60, 120 minutes or more. The $H_2O_2$ solution can be an about 0.5, 1, 2, 3, 4, 5, 6, 7, 8, 9, 10% or more solution of $H_2O_2$. The diatom microbubbler can be present at a concentration of about 0.5, 1, 2, 3, 4, 5, 6, 7, 8, 9, 10 or more mg $mL^{-1}$.

In an embodiment the diatom microbubbler can be mixed with the $H_2O_2$ solution and then contacted with the biofilm or biofouling condition. Alternatively, the diatom microbubbler and the $H_2O_2$ are contacted separately (but at about the same time, e.g. within about 1 or 30 seconds, or 1, 2, 3, 4, 5 minutes of each other) with the biofilm or biofouling condition. In an embodiment the method is performed a second, third, or fourth time with a fresh diatom microbubbler and fresh $H_2O_2$ solution.

The biofilm or biofouling condition can comprise one or more strains of bacteria, fungi, filamentous fungi, yeasts, algae, cyanobacteria, viruses, and protozoa and combinations thereof.

The biofilm or biofouling condition can be present in or on a non-living surface or in or on a living surface or organism. The diatom microbubbler and $H_2O_2$ solution can be contacted with the living or non-living surface.

The storage modulus of the biofilm or biofouling condition can be reduced by 20, 30, 40, 50, 60, 70, 80, 90, 95, 99% or more. The amount of extracellular polymeric substances (EPS) at the biofilm or biofouling condition can be reduced by 20, 30, 40, 50, 60, 70, 80, 90, 95, 99% or more. The amount of microorganisms at the biofilm or biofouling condition can be reduced by 20, 30, 40, 50, 60, 70, 80, 90, 95, 99% or more.

Extracellular polymeric substances (EPSs) are natural high molecular weight polymers secreted by microorganisms into their environment. EPSs are important in the establishment of the functional and structural integrity of biofilms. EPSs are comprised of various biomolecules, such as oligopeptides, lipopolysaccharides, proteins, lipids, and DNA. EPSs can be attached to the microorganism's outer surface or can be secreted into the environment. EPSs can comprise 50 to 90% of a biofilm's total organic matter.

Also provided is a method of making amine-substituted diatom biosilica particles. The method comprises contacting diatom biosilica and dopamine hydrochloride (in an about 2:1, 1.5:1, 2.5:1, 1:1, or 1:2 ratio) with water and stirring for about 0.5, 1, 2, or more hours at about room temperature to form a solution. Tris-buffer (at about 40, 50, or 60 mM) is added to the solution (in an amount of about ⅕, ¼, ⅓, or ½ of the amount of the water) and the solution is stirred until amine-substituted diatom biosilica particles are formed. The amine-substituted diatom biosilica particles can then be collected via, for example, centrifugation. The particles can be washed with water and vacuum desiccated. The amine-substituted diatom biosilica particles can then be reacted with a catalyst for decomposition of hydrogen peroxide. For example, reaction with a KMnO4 solution will result in $MnO_2$-PDA(polydopamine)-diatoms.

The embodiments illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the embodiments claimed. Thus, it should be understood that although the present description has been specifically disclosed by embodiments, optional features, modification and variation of the concepts herein disclosed may be resorted to by those skilled in the art, and that such modifications and variations are considered to be within the scope of these embodiments as defined by the description and the appended claims.

EXAMPLES

Example 1. Fabrication of the $MnO_2$-Diatom Bubbler

A $MnO_2$-diatom bubbler was fabricated using diatom particles doped with $MnO_2$ nanosheets. Amine-substituted diatom particles were prepared by the reaction with (3-aminopropyl)triethoxysilane (APTES, Sigma-Aldrich). First, 2 g of diatom particles were added to 60 mL of toluene in a three-necked round-bottomed flask fitted with a thermometer, a reflux condenser, and an $N_2$ gas tube. 0.6 mL of distilled water was added to the mixture and stirred for 2 h at room temperature. Then, 3.4 mL of APTES was added to the mixture, which was taken to reflux for 6 h at 60° C. Second, the mixture was cooled and washed with toluene, 2-propanol, and distilled water 3 times. The obtained sample was dried in a vacuum desiccator for 2 days. Finally, 0.1 g of amine-substituted diatoms were added to 1 mL of 50 mM potassium permanganate ($KMnO_4$, Sigma-Aldrich) solution and sonicated for 30 min at room temperature. Then, the samples were filtered and washed with distilled water and ethanol three times. The obtained sample was dried in an oven for 1 day at 60° C. Alternatively, $MnO_2$-diatom particles were fabricated via water-based method. Amine-substituted diatom particles were prepared by the reaction of self-polymerization of dopamine. First, 0.2 g of diatom particles and 0.1 g of dopamine hydrochloride (Sigma-Aldrich) were added to 320 mL of water in a beaker and stirred for 1 h at room temperature. Then, 80 mL of tris-buffer (50 mM, pH=8.5) was added into the mixture to induce the self-polymerization of dopamine on the surface of diatom particles. After stirring for 24 h at room temperature, the polydopamine-coated diatom particles were collected by centrifugation at 1000 rpm for 3 min, followed by washing with water for three times. The obtained particles were dried in a vacuum desiccator for 1 day. Finally, 0.1 g polydopamine-coated diatom particles were added to 10 mL of 50 mM $KMnO_4$ solution and stirred for 2 h at room temperature. Then, the samples were collected by centrifugation at 1000 rpm for 3 min and washed with water for three times to remove residue KMnO4. The obtained sample was dried in a vacuum desiccator for 1 day.

Example 2. Characterization of the $MnO_2$-Diatom Bubbler

Optical images and movies of diatom bubblers were obtained with the optical microscope (Leica DMIL). The SEM images and elemental mapping of microparticles were obtained with HITACHI S-4700 microscope operating at 2.0 kV. The TEM images were obtained using JEOL 2100 TEM with an accelerating voltage of 200 kV. The elemental analysis of manganese within the diatom bubbler was conducted by the inductively coupled plasma atomic emission spectroscopy (ICP/AES). The nitrogen adsorption-desorption isotherms were measured at 77 K with the Quantachrome NOVA 2200e surface area and pore size analyzer. The specific surface area was calculated with the Brunauer-Emmett-Teller (BET) equation from the adsorption and desorption curve in the relative pressure ($P/P_0$) range of 0.05-0.30. The pore volume and pore size distribution were calculated from the desorption curve by the Barrett-Joyner-Halenda (BJH) method in the relative pressure $P/P_0$ range of 0.05-0.99. The X-ray photoelectron spectroscopy (XPS) data was analyzed by Kratos Axis ULTRA. The powder X-ray diffraction data was obtained using the Rigaku Miniflex 600. The size distribution of microparticles was obtained by the image analysis with the ImageJ software. The speed of particles was measured by using the Fiji software. The mass of $O_2$ gas generated from the decomposition of $H_2O_2$ was quantified by adding 2-4 mg diatom bubbler to 2 mL of 3% $H_2O_2$ solution in a gas-sampling bottle and measuring the partial pressure of $O_2$ in the gas phase with the sensor (Vernier).

Example 3. Preparation of Microgrooved PDMS Substrates

First, the silicon master was fabricated using the photolithography technique. To begin with, the flat silicon wafer was washed and dried. Then, a photoresist (SU-8 2050, MicroChem Corporation) was spin-coated (100 µm thickness) onto the wafer to reach desired thickness. Next, the substrate underwent soft bake, UV exposure, and post-exposure bake. During the UV exposure step, a photo mask with the designed pattern was placed on the wafer to cure only the area of interests. After the curing process, the excess uncured photoresist was washed out. The master was silanized by treatment with a vapor of trichloro (1H,1H,2H,2H-perfluorooctyl)silane, Sigma-Aldrich) to create a hydrophobic surface. Second, PDMS pre-polymer (SYLGARD 184 Silicon Elastomer Kit, Dow Corning) and its curing agent were thoroughly mixed in the 1:10 mass ratio. After degassing, the pre-polymer solution was cast onto the silicon master with the desired feature on it. Then, it was cured at 60° C. for 2 hr. The cured PDMS with the desired pattern was gently peeled off from the master. The fabrication of the flat PDMS followed the same procedure. The only difference was that the pre-polymer solution was poured on the flat silicon wafer.

Example 4. Biofilm Growth on the PDMS Substrate

Microbial broths were prepared using LB Broth, Lennox media (Difco™). *Escherichia coli* (ATCC No. 25922) was grown in the LB Broth at 37° C. under shaking (100 rpm) until they reached the mid-logarithmic growth phase. The concentration of *E. coli* was adjusted to obtain an optical density of 0.07 at the wavelength of 600 nm on a microplate reader (TECAN, Switzerland). This optical density corresponds to the concentration of McFarland 1 solution ($3 \times 10^8$ CFU $mL^{-1}$). *E. coli* (250 µL, $3 \times 10^8$ CFU $mL^{-1}$). Flat or micro-grooved PDMS substrates were placed on the cell culture media in 24-well plates, while immersing only the groove parts in solution. After 24 h, the PDMS substrates were rinsed once with sterile PBS. Then, 250 µL of $3 \times 10^8$ CFU $mL^{-1}$ fresh *E. coli* suspension was additionally added to the PDMS substrates. This process was repeated every day for 9 days to allow for the biofilm formation. After 9 days, the PDMS substrates were rinsed with sterile PBS before being used for further analysis.

Example 5. Biofilm Removal from the PDMS Substrate

After 9 days culture, biofilms grown on PDMS substrates were treated by replacing the cell culture media with 600 µL of 3% $H_2O_2$ solution or the mixture of 3% $H_2O_2$ solution and the $MnO_2$-diatom bubblers. After 30 min, all the solution was removed and gently rinsed once with PBS before the analysis.

Example 6. Rheological Analysis of the Biofilm

Rheological properties of the biofilm samples grown on flat PDMS substrates were measured by strain-controlled oscillatory shear experiments using a rotational rheometer (ARES-G2, TA instrument). Oscillatory strain (amplitude)-sweep tests were performed to determine the storage (G') and loss modulus (G") with 25 mm diameter parallel plate geometry at a fixed frequency of 1 rad $sec^{-1}$. The dynamic moduli were measured with the biofilm on the PDMS substrate that is fixed to lower plate of the rheometer. All the analyses were conducted and averaged from the results of five different measurements with different samples.

Example 7. Viability Assay of the Biofilm

The Cell Titer-Blue cell viability assay was performed to quantitatively analyze live *E. coli* cells attached to the PDMS. *E. coli* in the LB Broth, Lennox media (Difco™) (100 µL, $3 \times 10^8$ CFU $mL^{-1}$) were seeded onto PDMS substrates cured in 24-well plates and cultured at 37° C. for 9 days. After 9 days, 600 µL of 3% $H_2O_2$ solution or the mixture of 3% $H_2O_2$ and the $MnO_2$-diatom bubbler particles was added to the biofilms for 30 min. The surfaces were washed twice with sterile PBS, followed by incubation with 100 µL of PBS and 20 µL of Cell Titer Blue Reagent at 37° C. for 6 h. The fluorescence intensity of resorufin resulting from reduction of resazurin by dehydrogenases of viable cells was determined at the excitation wavelength of 560 nm and the emission wavelength of 590 nm using the microplate reader. The experiment was conducted in replicates of 3.

Example 8. Fluorescence Imaging of the Biofilm

Proteins in the biofilm were stained by incubating them for 1 h at room temperature with 500 μL of 10 mg mL$^{-1}$ fluorescein isothiocyanate (Sigma-Aldrich, USA) in 0.1 M NaHCO$_3$ buffer to conjugate the dye onto deprotonated amino groups. Then, the biofilm was washed with PBS before staining polysaccharides in the biofilm. Polysaccharides in the biofilms were stained by incubating the biofilm for 2 h with 500 μL of 250 μg mL$^{-1}$ fluorescently-labeled lectin concanavalin A conjugated with tetramethyl rhodamine (Molecular Probes, USA). The chemical binds to α-glucopyranosyl and α-mannopyranosyl sugar residues. Subsequently, the biofilms were washed with PBS before incubating them for 2 h with 500 μL of 300 μg mL$^{-1}$ fluorescent brightener 28 (MP Biomedicals, LLC, USA), which binds to β-linked polysaccharides. The biofilms were washed with PBS. Then, the samples were mounted on glass slides and observed with a laser scanning confocal microscope (Zeiss LSM 700, Germany, a 200× objective).

Figure 5:
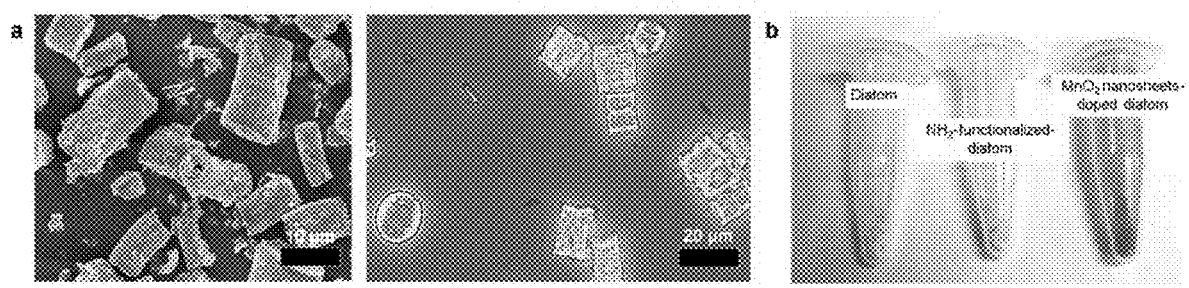
FIG. 5. (a) SEM (left) and optical (right) images of diatom bubblers doped with MnO$_2$ nanosheets. (b) Photo images of diatom, amine-substituted diatom skeleton, and MnO$_2$ nanosheets-doped diatom skeleton (diatom bubbler) powders.

Example 9. Synthesis and Characterization of MnO$_2$ Nanosheets-Doped Diatom Bubbler The diatom particles used in this study have the hollow cylinder morphology with 10 μm-diameter and 18 μm-length while the wall exhibits many pores with an average diameter of 500 nm (FIGS. 1a and 5a). First, the diatom surface was functionalized with (3-aminopropyl) triethoxysilane (APTES) to present amine groups (FIG. 1b). Then, MnO$_2$ nanosheets were doped on the amine-functionalized diatom by reducing potassium permanganate (FIGS. 1b and 5b). The loading amount of MnO$_2$ nanosheets was approximately 2.5 wt %, according to the inductively-coupled plasma-atomic emission spectroscopy analysis. The elemental mapping of Mn in SEM confirms that the MnO$_2$ nanosheets are loaded on the diatom particles (FIG. 1c). The high-resolution transmission electron microscopic (TEM) images show that MnO$_2$ nanosheets are located on the porous wall surfaces (FIG. 1d). According to the N$_2$ adsorption analysis, the specific surface area and pore volume of MnO$_2$ nanosheets-doped diatom (24 m$^2$ g$^{-1}$ and 0.057 cm$^3$ g$^{-1}$) are comparable to those of bare diatom particles (27 m$^2$ g$^{-1}$ and 0.076 cm$^3$ g$^{-1}$). This result indicates that most pores of the diatom particle were still open after deposition of MnO$_2$ nanosheets (FIG. 1e). On the other hand, the powder x-ray diffraction pattern of the MnO$_2$ nanosheets-doped diatom exhibits no difference from bare diatom. This result reveals that the doped MnO$_2$ nanosheets on diatom particles are in an amorphous state (FIG. 1f).

Figure 2:
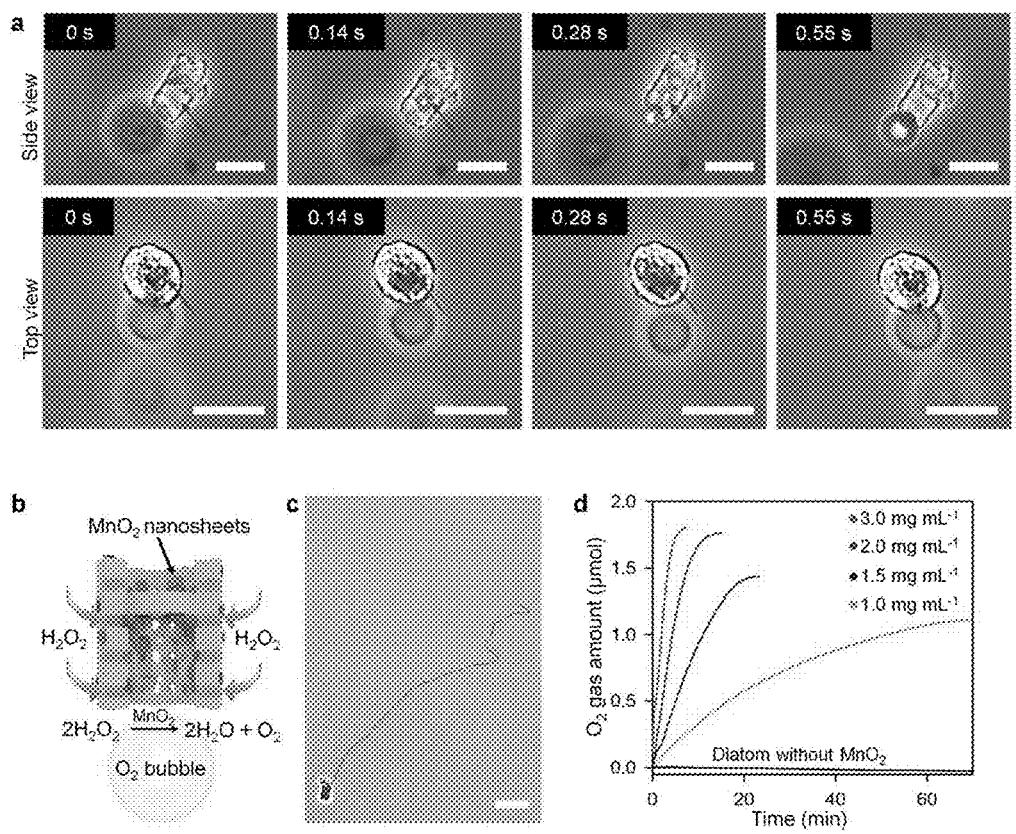
FIG. 2. Self-locomotion of MnO$_2$ nanosheets-doped diatom in H$_2$O$_2$ solution. (a) Time-lapse images of the microbubble generated from the diatom in 3% H$_2$O$_2$ solution (Scale bar=10 μm). (b) Schematic illustration of the mechanism by which the MnO$_2$-diatom produces O$_2$ bubbles and self-propels. (c) Tracking of the self-locomotion of MnO$_2$-diatom bubbler added to H$_2$O$_2$ solution (Scale bar=20 μm). (d) Quantification of O$_2$ gas generated from 3% H$_2$O$_2$ solution mixed with varying amount of the MnO$_2$-diatom bubbler. Unmodified diatom was included as a control.
Figure 6:
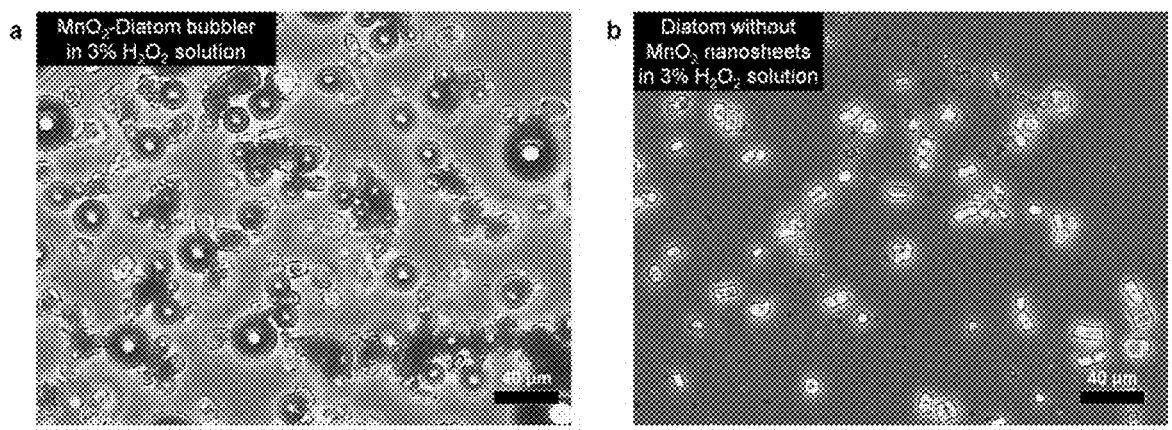
FIG. 6. (a) When the MnO$_2$-diatom bubbler particles were added to the 3% H$_2$O$_2$ solution, the particles instantly generate bubbles. (b) In comparison, diatom skeletons without MnO$_2$ nanosheets do not generate any bubbles.
Figure 7:
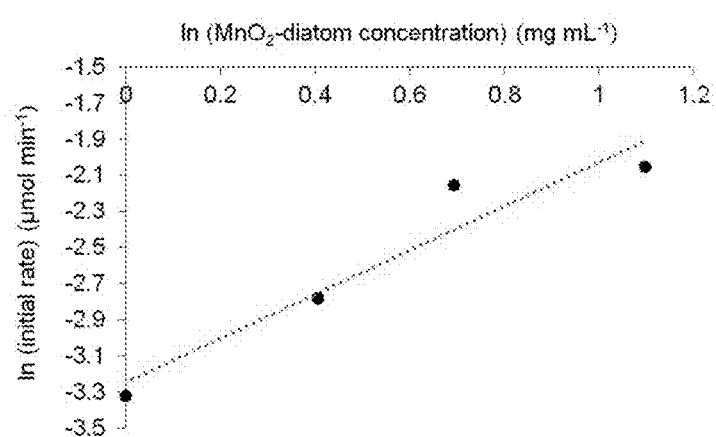
FIG. 7. Plot of ln (initial rate) versus ln (MnO$_2$-diatom concentration). All other conditions are same as FIG. 2d.

The MnO$_2$ nanosheet-doped diatom (MnO$_2$-diatom) instantly generated O$_2$ microbubbles in a 3% H$_2$O$_2$ solution while the diatom without MnO$_2$ nanosheets did not show any bubbles (FIG. 6). Interestingly, O$_2$ bubbles are continuously ejected from the hollow hole of the MnO$_2$-diatom as shown in the time-lapse images (FIG. 2a). The bubbles showed a uniform diameter of 12 μm which is similar to that of diatom. From this result, we assume that H$_2$O$_2$ molecules in the solution diffuse through nanopores of the diatom wall and quickly decompose to generate O$_2$ gas by reacting with MnO$_2$ nanosheets (FIG. 2b). The generated O$_2$ gas bubbles start to nucleate and form microbubbles inside the hollow space of a diatom. As the bubbles build up the pressure, the diatom bubbler continuously jets microbubbles through the hollow channel. The ejection of bubble from the hollow channel allows the continuous diffusion of H$_2$O$_2$ molecules and generation of the microbubbles. Due to the continuous inward diffusion, no microbubbles were formed on the outer surface of MnO$_2$-diatoms. Subsequently, the MnO$_2$-diatom moved at a rate of 60 μm s$^{-1}$ (FIG. 2c). The O$_2$ gas generation from the diatom bubbler was also confirmed with the oxygen sensor. The initial reaction rates with different MnO$_2$-diatom concentrations were calculated to determine the order of reaction (FIG. 2d and FIG. 7). The order of the reaction was approximately 1.2 with respect to the MnO$_2$-diatom concentration.

Alternatively, MnO$_2$-diatom particles were fabricated through the self-polymerization of dopamine. First, the diatom particles were modified with a layer of binder, polydopamine (PDA), for the following immobilization of MnO$_2$ on its surface. The PDA-diatom particles (FIG. 13b) were obtained through self-polymerization of dopamine on the surface of diatom particles in a weak alkaline tris buffer solution (pH=8.5). Since the concentration of dopamine played an important role in the surface modification process, the PDA coating was optimized with three different concentrations: 1, 0.25, and 0.05 mg/mL. High concentration of dopamine (i.e. 1 mg/mL) resulted in lots of precipitates of PDA nanoparticles in bulk solution, which also blocked the holes on the surface of diatom particles. On the other hand, inadequate PDA was coated on the surface of diatom particles when using low concentration of dopamine (i.e. 0.05 mg/mL). Thus, the concentration of dopamine was optimized at 0.25 mg/mL in this work to ensure sufficient PDA coated on the surface without blocking the holes. The thickness of PDA layer coated on the wall of diatom particles is around 50 nm, corresponding to the saturation of PDA coating in the literature. Then, PDA-diatom particles were decorated with MnO$_2$ (MnO$_2$-PDA-diatom) via the reduction of MnO$_4$$^-$, following the reaction equation:

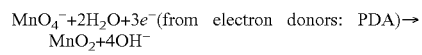

$$MnO_4^- + 2H_2O + 3e^- \text{(from electron donors: PDA)} \rightarrow MnO_2 + 4OH^-$$

The PDA layer served as reducing agent and binder to reduce MnO$_4$$^-$ into MnO$_2$ in situ and immobilized MnO$_2$ on the surface of diatom particles. The elemental mapping images show uniform distribution of Mn on the surface and the high-resolution TEM images further indicate that MnO$_2$ is located on the top of PDA layer. The loading amount of Mn element confirmed by inductively coupled plasma-atomic emission spectroscopy is approximately 18.2% by mass. The whole modification process could also be verified by the color changes from white (diatom) to black (PDA) and eventually to brown (MnO$_2$).

Next, X-ray photoelectron spectroscopy (XPS) analysis was conducted to confirm the chemical composition on the surface of diatom particles. An XPS survey spectrum of pristine diatom, PDA-diatom, and MnO$_2$-PDA-diatom particles was completed. The peaks of Si 2s (153.0 eV) and Si 2p (100.2 eV) in pristine diatom are consistent with biosilica SiO$_2$ composition. Moreover, these two Si peaks sharply decrease in PDA-diatom and MnO$_2$-PDA-diatom, which indicates the surface of diatom is covered with PDA layer and MnO$_2$. To verify the PDA coating on diatom particles, the high-resolution N 1s XPS spectrum of PDA-diatom was analyzed. The N 1s peak at 400.0 eV in PDA-diatom was fitted into three peaks at 398.6 eV, 399.9 eV, and 401.9 eV, corresponding to tertiary/aromatic (R—N=), secondary (R$_2$—N—H), and primary (R—NH$_2$) amine functionalities in PDA chemical structure. These three amine groups are 11.50%, 74.21%, 14.29% respectively and are consistent with the composition of PDA in the previous report. In contrast, there was no N 1s signal in $MnO_2$-PDA-diatom, suggesting the deposition of $MnO_2$ on the top of PDA layer. The two peaks in Mn 2p spectrum at 642.1 eV (Mn $2p_{3/2}$) and 653.8 eV (Mn $2p_{1/2}$) with spin-energy separation of 11.7 eV and the spin-energy separation of 4.7 eV in Mn 3s spectrum also indicate the existence of $Mn^{4+}$ in the composition.

Example 10. Active Biofilm Removal with Diatom Bubbler

Figure 3:
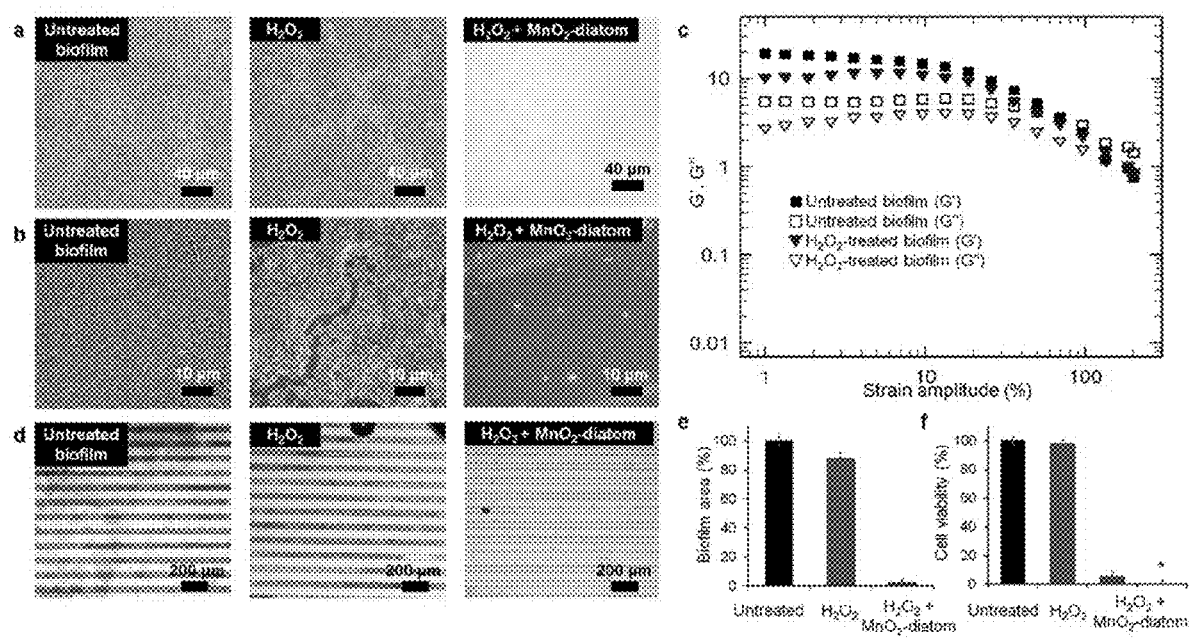
FIG. 3. Effects of the MnO$_2$-diatom bubbler on the biofilm formed on flat or microgrooved PDMS substrate. (a, b) Optical (a) and SEM (b) images of E. coli biofilm grown on flat PDMS substrates before and after treatments of 3% H$_2$O$_2$ solution without and with MnO$_2$-diatom. (c) Storage modulus (G') and loss modulus (G") of the biofilm as a function of the oscillatory strain amplitude. d) Optical image of the biofilm formed on microgrooved PDMS substrates (50 μm width and 100 μm depth) before and after treatments of 3% H$_2$O$_2$ solution without and with MnO$_2$-diatom. e) Quantified biofilm area on microgrooved PDMS substrate. f) The viability of E. coli in the biofilm on the PDMS substrate. The secondary treatment with diatom bubbler led to the death of 99.9% of cells, which is marked with an asterisk (*).
Figure 8:
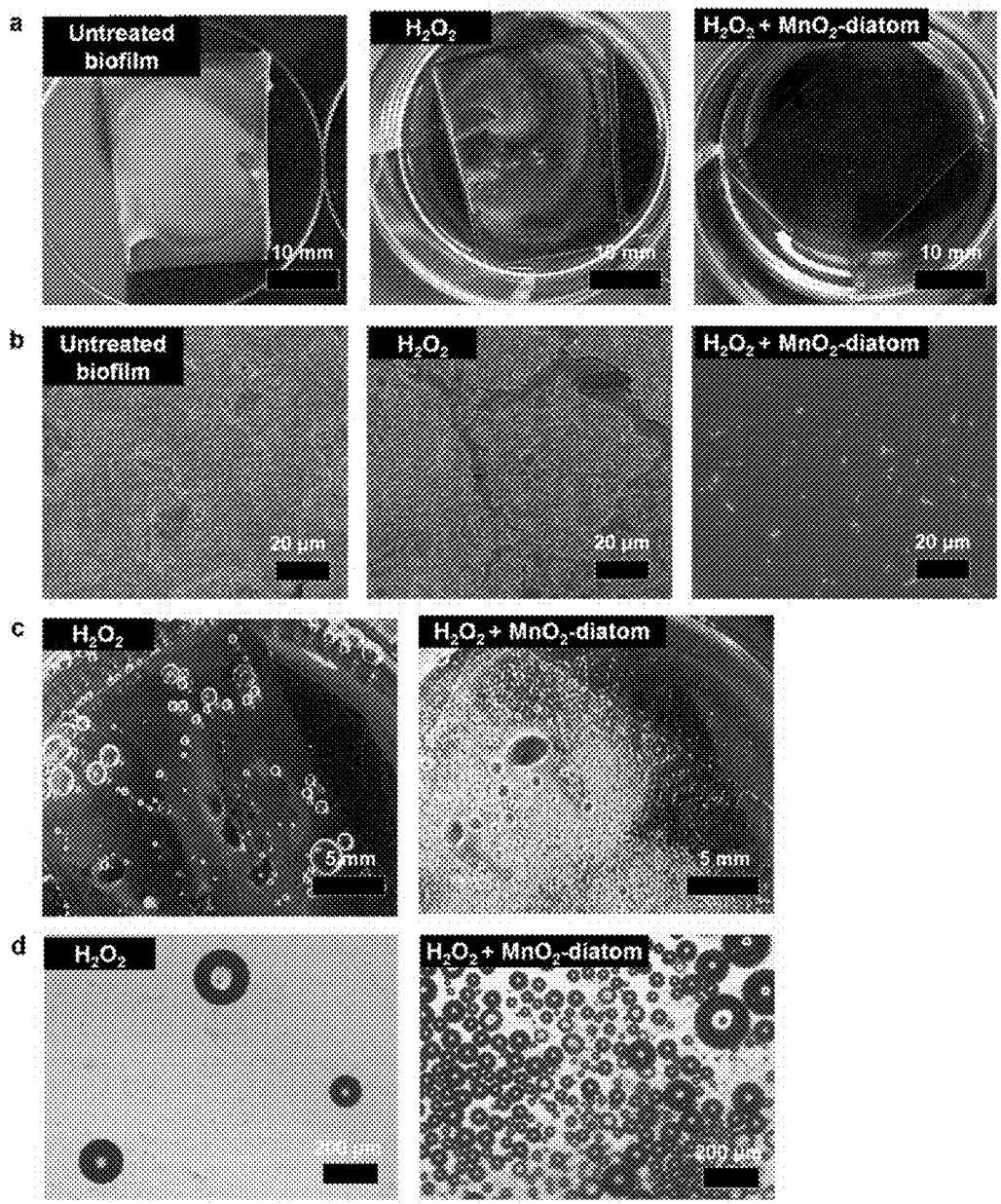
FIG. 8. (a, b) Optical (a) and SEM (b) images of E. coli biofilm grown on flat PDMS substrate before and after treatment. (Images on the 1st column) Untreated biofilm covers the substrate surface. (Images on the 2nd column). Exposure of the biofilm to 3% H$_2$O$_2$ solution for 30 min damages the biofilm minimally. (Images on the 3rd column) the mixture of 3% H$_2$O$_2$ and the MnO$_2$-diatom bubbler cleans the fouled PDMS substrate, thus leaving a minimal number of cells on the PDMS substrate. (c, d) (Left images) Photograph (c) and optical microscopic image (d) of the macro-sized bubbles formed on the biofilm treated with 3% H$_2$O$_2$ solution. (Right images) Photograph (c) and optical microscopic image (d) of the microbubbles formed within the biofilm treated with the mixture of 3% H$_2$O$_2$ and the MnO$_2$-diatom bubbler for 30 min.

Next, the extent to which the $MnO_2$-diatom bubbler cleans the flat polydimethylsiloxane (PDMS) substrate fouled by the Gram-negative *Escherichia coli* (*E. coli*) biofilm was examined. First, the fouled PDMS substrate was exposed to 3% $H_2O_2$ solution for 30 minutes. This procedure resulted in macro-sized bubbles with a few hundred micrometers above the biofilm because the catalase in *E. coli* decomposed $H_2O_2$ into $O_2$ gas. Approximately 80% of the biofilm remained on the PDMS substrates when they were examined with microscope images (FIGS. 3a, 3b, 8). According to the oscillatory shear test, the storage modulus of the biofilm decreased from 20 to 10 Pa (FIG. 3c). However, $H_2O_2$-treated biofilm showed a high yield strain, indicating that the structure of biofilm matrix was retained even after $H_2O_2$ treatment, suggesting no significant change to the structure. In contrast, the $MnO_2$-diatom bubbler mixed with $H_2O_2$ solution generated microbubbles on the fouled PDMS substrate and removed most of the biofilm within 30 minutes (FIGS. 3a, 3b, 8). Because there was no remaining biofilm on the substrate, it was not possible to measure the rheological property of the biofilm after the treatment of $MnO_2$-diatom bubbler.

Figure 9:
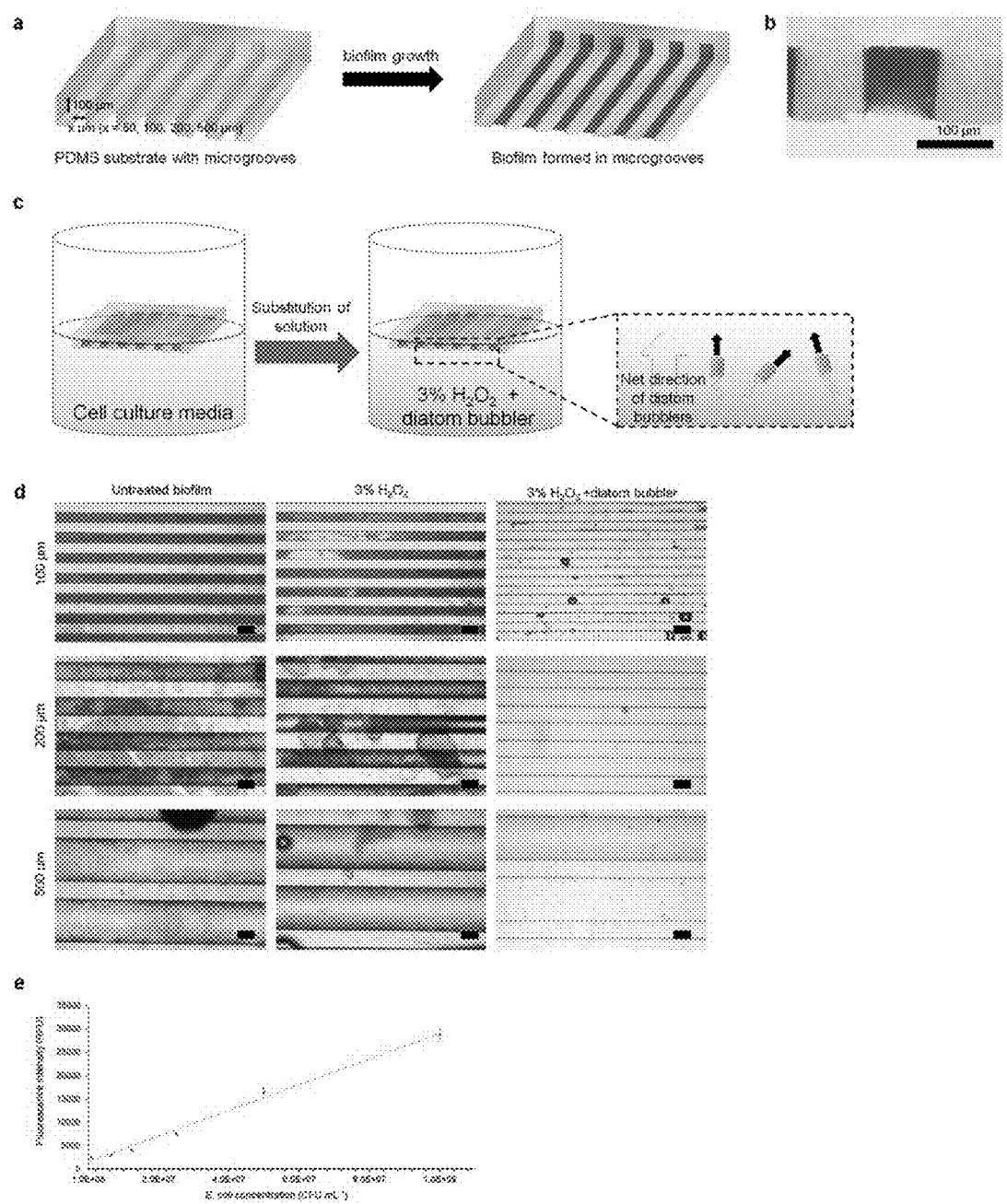
FIG. 9. (a) Schematic illustration of the process to grow biofilm in microgrooves of the PDMS substrates. (b) Optical microscopic image of the side-view of biofilm in microgrooves of the PDMS substrate. (c) Schematic illustration for the biofilm removal process from the microgrooves of PDMS substrate. (d) Optical images of E. coli biofilm grown on PDMS substrates with microgrooves width of 100, 200, and 500 μm. Dark area in images represent the biofilm. Exposure of the biofilm to 3% H$_2$O$_2$ solution for 30 min removed the biofilm moderately. The efficiency to remove biofilm decreases with the smaller microgroove width. In contrast, the mixture of 3% H$_2$O$_2$ and the MnO$_2$-diatom bubbler removed the biofilm from microgrooves, independent of the microgroove width. (e) Calibration curve for the fluorescence intensity of resorufin modulated with different concentrations of E. coli.
Figure 10:
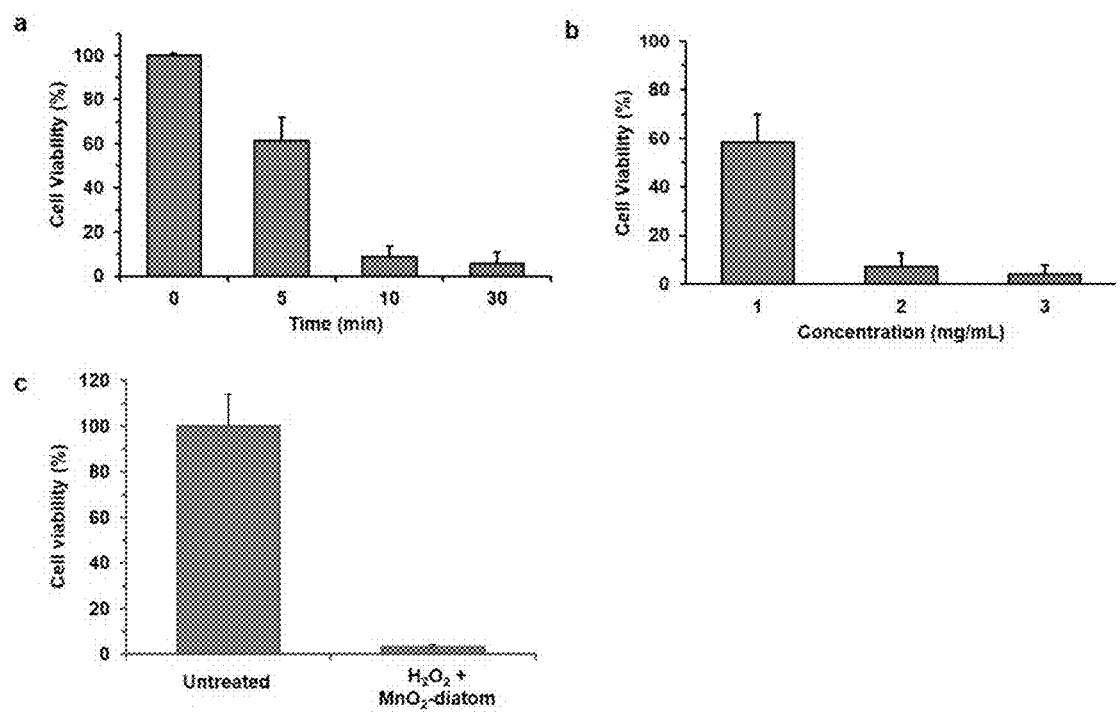
FIG. 10. (a, b) The viability of E. coli in the biofilm remained on the PDMS substrate. (a) The biofilm was exposed to 3% H$_2$O$_2$ solution mixed with MnO$_2$-diatom bubblers for different period. The concentration of MnO$_2$-diatom bubblers was kept constant at 1.0 mg mL$^{-1}$ concentration. (b) The biofilm was exposed to 3% H$_2$O$_2$ solution mixed with different concentrations of MnO$_2$-diatom bubblers for 5 min. (c) The viability of E. coli cells in supernatant solution from the detached biofilm after 30 min treatment time.

The capability of the $MnO_2$-diatom bubbler to invade and remove the biofilm formed in a confined space was examined. To simulate the biofilm in confined spaces, we used the micro-grooved PDMS substrates with controlled widths of 50, 100, 200, and 500 μm and depth of 100 μm. The biofilms were formed exclusively within microgrooves regardless of width. The confinement effect of biofilm formation could be explained by cell-to-cell signaling and interaction among bacterial cell clusters. Most of the biofilms in microgrooves of PDMS substrates were removed 30 minutes after the mixture of 3% $H_2O_2$ and the $MnO_2$-diatom was added (FIG. 3d FIG. 9). In contrast, the biofilms still lingered on the microgrooves after 3% $H_2O_2$ solution treatment (FIG. 3d and FIG. 9). The quantitative analysis of the images revealed that the $MnO_2$-diatom treatment cleaned 8-fold larger surface area than $H_2O_2$ solution treatment alone (FIG. 3e). The cell viability gradually decreased with the time at the concentration of the $MnO_2$-diatom bubbler being 1.0 mg $mL^{-1}$ in 3% $H_2O_2$ solution (FIG. 10a). On the other hand, increasing the concentration of the $MnO_2$-diatom bubblers from 1.0 to 3.0 mg $mL^{-1}$ decreased the cell viability a lot within 5 min (FIG. 10b). As a result, 95% of *E. coli* cells in the biofilm lost viability after the $MnO_2$-diatom bubbler treatment, while most of the cells in the biofilm treated only with the $H_2O_2$ solution remained viable (FIG. 3f). Moreover, the secondary treatment with a fresh mixture of 3% $H_2O_2$ and the $MnO_2$-diatom bubblers led 99.9% of *E. coli* cells to lose viability. In addition, the $MnO_2$-diatom bubbler was effective to reduce the viability of *E. coli* in the detached biofilm (FIG. 10c).

Figure 11:
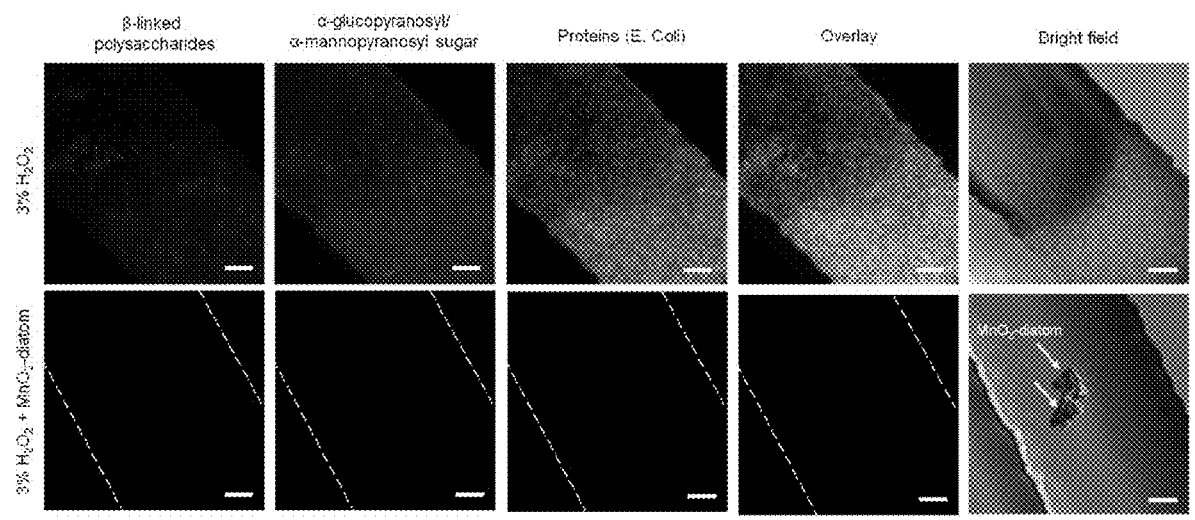
FIG. 11. (1$^{st}$ row images) Biofilm exposed to the 3% H$_2$O$_2$ solution for 30 minutes; (2nd row images) biofilm exposed to the mixture of H$_2$O$_2$ and diatom bubbler for 30 minutes (Scale bar=10 μm). Two MnO$_2$-diatom particles are shown inside the microgroove in bright field image.

The structure of biofilms in microgrooves before and after the treatment was analyzed with fluorescence images (FIGS. 4a and 11). The EPS matrix of untreated biofilm comprises β-linked polysaccharides (blue-colored) and α-glucopyranosyl and α-mannopyranosyl sugar residues (red-colored). Extracellular proteins (green-colored) were localized mostly on *E. coli* cell walls. Even after 3% $H_2O_2$ solution treatment, a large amount of EPS and *E. coli* remained in the microgrooves, as quantified with the mean fluorescence intensity across the microgrooves. In contrast, the mixture of $H_2O_2$ and $MnO_2$-diatom bubblers removed all EPS and *E. coli* cells, as confirmed with no fluorescence yield from the substrate. This result indicates that $MnO_2$-diatom bubbler treatment could prevent biofilm from recovering because there was no residual amount of EPS and bacterial cells at all after the treatment.

Example 11. Mechanism Study of Active Biofilm Removal

The intermediate stage of treatment was monitored to address the active cleaning mechanism of the $MnO_2$-diatom bubbler in more detail. The self-locomotive diatom bubblers infiltrated the biofilm and continuously produced microbubbles within the biofilm. These microbubbles merged and burst to deform and fracture the biofilm until they collapsed. As a result, circular- or ellipsoidal-shaped damages could be found in between the biofilm while the diatom particles are observed inside the biofilm matrix (FIGS. 4b and 4c). In contrast, the biofilm exposed to the $H_2O_2$ solution exhibited macro-sized bubbles with a few hundred micrometers stayed outside the substrate due to the diffusion limitation (FIG. 4c).

The energy of microbubbles used to rupture the biofilm was estimated by calculating the change in the surface energy of microbubbles. Yasui, K., Bubble Dynamics. In Acoustic Cavitation and Bubble Dynamics, Springer: 2018; pp 37-97. The coalescence of the microbubbles is considered as a process to minimize surface energy. Massey, B. S.; Ward-Smith, J., Mechanics of fluids. Crc Press: 1998; Vol. 1. During this coalescence, the surface energy is released in the form of mechanical energy. Since initially formed microbubbles have a nearly spherical shape, the mechanical energy is calculated from surface energy difference between initial and final states as follows, $$\Delta E = \Sigma 4\pi r_i^2 \Gamma - \Sigma 4\pi r_f^2 \Gamma \quad (1)$$

where $r_i$, $r_f$, and $\Gamma$ represent the radius of bubbles at the initial state, the radius of bubbles at the final states, and the surface tension value for the water-air interface, respectively. The E was calculated based on the results observed in optical microscope (FIG. 4d). The calculated $\Delta E$ was compared to the mechanical work required to deform the biofilm in the observed area. Using the storage modulus (G') of the untreated biofilm shown in FIG. 3c, the required mechanical work per unit volume ($E_{req}$) is given as, $$E_{req} = \int F ds = \int_0^\gamma G'(\gamma) \gamma d\gamma \quad (2)$$

where γ is the applied strain. According to the calculation (Supporting Information), the mechanical energy attained from the coalescence of microbubbles ($3.02 \times 10^{-10}$ J) far outweighs $E_{req}$ ($2.03 \times 10^{-12}$ J). The calculations are shown below:

Surface Energy:

$$\Delta E = \sum 4\pi r_i^2 \Gamma - \sum 4\pi r_f^2 \Gamma = \left(\sum 4\pi r_i^2 - \sum 4\pi r_f^2\right)\Gamma$$
$$= [(1.28 \times 10^{-9} - 8.70 \times 10^{-9})m^2] \times 72.9 \times 10^{-3} Nm^{-1}$$
$$= 3.02 \times 10^{-10} J$$

Energy Required to Deform Biofilm:

$$E_{req} = V = \int_0^\gamma G'(\gamma)\gamma d\gamma \times V = \int_0^{\gamma y} G'(\gamma)\gamma d\gamma \times A \times l$$
$$= 4.05 Nm^{-2} \times [(100 \times 10^{-6}) \times (50 \times 10^{-6})]m^2 \times (100 \times 10^{-6})m$$
$$= 2.03 \times 10^{-12} J$$

$r_i$, $r_f$: Radius of bubbles at the initial and final points
Γ: Surface tension of water-air interface (N m$^{-1}$)→72.9 mN m$^{-1}$
A: Observed area (m$^2$)→[(50×10$^{-6}$)×(100×10$^{-6}$)]m$^2$
l: Groove depth (m)→(100×10$^{-6}$)m
G': Elastic (storage) modulus (N/m$^2$) from FIG. 2c
γ: Applied strain→from 0 to 2.0 (high enough strain for full destruction of biofilm matrix)

2.0 was determined as the upper limit of strain because, at this strain amplitude, the dynamic moduli are about ten times smaller than the dynamic moduli of the untreated biofilm. Further increase in strain beyond this value does not result in remarkable increase in required work as the storage modulus is very small.

|  | radius (m) | surface area (m$^2$) |
|---|---|---|
| initial (4.3 s) | 10.1 × 10$^{-6}$ | 1.28 × 10$^{-9}$ |
|  | 9.45 × 10$^{-6}$ | 1.12 × 10$^{-9}$ |
|  | 8.18 × 10$^{-6}$ | 8.41 × 10$^{-10}$ |
|  | 6.42 × 10$^{-6}$ | 5.18 × 10$^{-10}$ |
|  | 5.76 × 10$^{-6}$ | 4.17 × 10$^{-10}$ |
|  | 6.21 × 10$^{-6}$ | 4.85 × 10$^{-6}$ |
|  | 26.6 × 10$^{-6}$ | 8.17 × 10$^{-9}$ * |
| final (5.6 s) | 29.0 × 10$^{-6}$ | 8.70 × 10$^{-9}$ * |

* Calculated by ellipsoidal surface area.

$$\text{Surface area} \approx 4\pi \left( \frac{(ab)^{1.6} + (ac)^{1.6} + (bc)^{1.6}}{3} \right)^{1/1.6}$$

This result indicates that the fusion between microbubbles from the diatom bubbler generates mechanical energy high enough to rupture the biofilm, confirming the experimental observations. The MnO$_2$-diatom bubbler can remove the biofilm formed even in complex confined spaces (FIG. 4e). The use of 3% H$_2$O$_2$ solution may cause corrosion on the metallic substrates. However, the MnO$_2$-diatom particles decompose H$_2$O$_2$ gradually for the microbubble generation. Consequently, the MnO$_2$-diatom bubbler not only improves anti-bacterial activity of H$_2$O$_2$ during treatment period but also neutralize H$_2$O$_2$ in the end, which decrease the possibility of substrate corrosion.

We claim:

1. A diatom microbubbler configured to generate oxygen gas bubbles comprising diatom biosilica linked to a catalyst for the decomposition of hydrogen peroxide (H$_2$O$_2$).

2. The diatom microbubbler of claim 1, wherein the catalyst for the decomposition of hydrogen peroxide is (1) manganese oxide (MnO$_2$), platinum (Pt), CuO (copper II oxide), or zinc peroxide (ZnO$_2$) particles or nanosheets, or (2) catalase.

3. The diatom microbubbler of claim 1, wherein the diatom biosilica is linked to MnO$_2$ nanosheets.

4. The diatom microbubbler of claim 1, wherein the diatom biosilica is linked to MnO$_2$ via a polydopamine linker.

5. The diatom microbubbler of claim 1, wherein the diatom biosilica is cylinder-shaped with a hollow central bore.

6. The diatom microbubbler of claim 1, wherein the diatom microbubbler is configured to self-propel.

7. A method of reducing a biofilm or biofouling condition comprising contacting:
   (a) a diatom microbubbler comprising diatom biosilica linked to a catalyst for the decomposition of H$_2$O$_2$; and
   (b) a H$_2$O$_2$ solution;
   with the biofilm or biofouling condition such that oxygen gas bubbles are generated for a period effective to reduce reproduction of microorganism or to reduce numbers of microorganisms in or on the biofilm or biofouling condition.

8. The method of claim 7, wherein the catalyst for the decomposition of hydrogen peroxide is (1) manganese oxide (MnO$_2$), platinum (Pt), CuO (copper II oxide), or zinc peroxide (ZnO$_2$) particles or nanosheets, or (2) catalase.

9. The method of claim 7, wherein the H$_2$O$_2$ solution is a 1-5% solution of H$_2$O$_2$.

10. The method of claim 7, wherein the diatom microbubbler is present at a concentration of 0.5 to 5.0 mg mL$^{-1}$.

11. The method of claim 7, wherein the diatom microbubbler is mixed with the H$_2$O$_2$ and then contacted with the biofilm or biofouling condition.

12. The method of claim 7, wherein the diatom microbubbler and the H$_2$O$_2$ are contacted separately with the biofilm or biofouling condition.

13. The method of claim 7, wherein the biofilm or biofouling condition comprises one or more strains of bacteria, fungi, filamentous fungi, yeasts, algae, cyanobacteria, viruses, and protozoa and combinations thereof.

14. The method of claim 7, wherein the biofilm or biofouling condition comprises one or more strains of bacteria.

15. The method of claim 7, wherein the biofilm or biofouling condition is present in or on a non-living surface.

16. The method of claim 7, wherein the biofilm is present in or on a living surface or organism.

17. The method of claim 16, wherein the biofilm is present at a wound site or infection site in a mammal.

18. The method of claim 7, wherein the storage modulus of the biofilm or biofouling condition is reduced by 50% or more.

19. The method of claim 7, wherein the method is performed a second time with a fresh diatom microbubbler and fresh H$_2$O$_2$ solution.

20. The method of claim 7, wherein the amount of extracellular polymeric substances (EPS) of the biofilm is reduced by 50% or more.

21. The method of claim 7, wherein the diatom microbubbler self-propels through or around the biofilm or biofouling condition.

22. A method for making amine-substituted diatom biosilica particles comprising:
   (a) contacting diatom biosilica and dopamine hydrochloride with water and stirring to form a solution;
   (b) adding tris-buffer to the solution and stirring until amine-substituted diatom biosilica particles are formed; and collecting the amine-substituted diatom biosilica particles.

* * * * *